United States Patent
Keri et al.

(10) Patent No.: US 7,645,876 B2
(45) Date of Patent: *Jan. 12, 2010

(54) PROCESSES FOR PRODUCING CRYSTALLINE MACROLIDES

(75) Inventors: Vilmos Keri, Debrecen (HU); Istvan Melczer, Debrecen (HU); Adrienne Kovacsne-Mezei, Debrecen (HU)

(73) Assignee: TEVA Gyógyszergyár Zártkörüen Müködö Részvénytársaság, Debrecen (HU)

( * ) Notice: Subject to any disclaimer, the term of this patent is extended or adjusted under 35 U.S.C. 154(b) by 0 days.

This patent is subject to a terminal disclaimer.

(21) Appl. No.: 11/293,747

(22) Filed: Dec. 1, 2005

(65) Prior Publication Data

US 2006/0135548 A1    Jun. 22, 2006

Related U.S. Application Data

(60) Provisional application No. 60/632,372, filed on Dec. 1, 2004, provisional application No. 60/633,926, filed on Dec. 6, 2004, provisional application No. 60/641,697, filed on Jan. 5, 2005, provisional application No. 60/641,868, filed on Jan. 5, 2005, provisional application No. 60/641,869, filed on Jan. 5, 2005, provisional application No. 60/662,440, filed on Mar. 16, 2005, provisional application No. 60/705,681, filed on Aug. 3, 2005, provisional application No. 60/709,160, filed on Aug. 17, 2005.

(51) Int. Cl.
   *C07D 498/18* (2006.01)
(52) U.S. Cl. ...................................... 540/456
(58) Field of Classification Search .................. 540/456; 514/183, 291, 411
   See application file for complete search history.

(56) References Cited

U.S. PATENT DOCUMENTS

| 3,244,592 | A | | 4/1966 | Arai et al. |
| 5,508,398 | A | * | 4/1996 | Gletsos ...................... 540/456 |
| 6,268,489 | B1 | * | 7/2001 | Allen et al. ................. 536/7.4 |
| 6,423,722 | B1 | * | 7/2002 | Dosenbach et al. ......... 514/291 |
| 6,576,259 | B2 | * | 6/2003 | Yamashita et al. .......... 424/468 |
| 6,620,325 | B2 | | 9/2003 | Fuenfschilling et al. |
| 6,706,727 | B1 | | 3/2004 | Fleissner et al. |
| 7,232,486 | B2 | * | 6/2007 | Keri et al. ..................... 117/68 |
| 7,439,252 | B2 | * | 10/2008 | Keri et al. ................... 514/291 |
| 2008/0269479 | A1 | * | 10/2008 | Buchta et al. ............... 540/456 |

FOREIGN PATENT DOCUMENTS

| EP | 0 323 865 A1 | 7/1989 |
| EP | 0 427 680 A1 | 5/1991 |
| EP | 0 427 680 B1 | 5/1991 |
| EP | 0 480 623 A1 | 4/1992 |
| EP | 1 234 833 A2 | 8/2002 |
| WO | WO 93/04679 A1 | 3/1993 |
| WO | WO-93/04680 A1 | 3/1993 |
| WO | WO 93/18050 A1 | 9/1993 |
| WO | WO-99/01458 A1 | 1/1999 |
| WO | WO-01/90110 A1 | 11/2001 |
| WO | WO 03/063821 A2 | 8/2003 |
| WO | WO 03/063822 A2 | 8/2003 |
| WO | WO 2004/089958 A2 | 10/2004 |
| WO | WO 2005/010015 A1 | 2/2005 |
| WO | WO 2005/117837 A1 | 12/2005 |
| WO | WO 2006/031664 A1 | 3/2006 |

OTHER PUBLICATIONS

Griffiths, C.E., "Ascomycin: An Advance in the Management of Atopic Dermatitis." *British Journal of Dermatology*, (2001) vol. 144, p. 679-681.

Kessler, H., et al., "Structure of Rapamycin: An NMR and Molecular-Dynamics Investigation" Helvetica Chimica Acta, (1993)vol. 76, p. 117-130.

Brittain, H.G. (Editor) "Polymorphism in Pharmaceutical Solids" Drugs and the Pharmaceutical Sciences vol. 95, (1999) Marcel Dekker, Inc. New York, New York.

Remington, J. P. (Editor) "The Science and Practice of Pharmacy", vol. II, Chapter 92, "Oral Solid Dosage Forms", p. 1615-1649 (1995) Mack Publishing Company, Easton, Pennsylvania.

Vu, L: "Amorphous Pharmaceutical Solids: Preparation, Characterization and Stabilization." Advanced Drug Delivery Reviews, (2001) vol. 48, p. 27-42.

\* cited by examiner

*Primary Examiner*—Shaojia Anna Jiang
*Assistant Examiner*—Eric S Olson
(74) *Attorney, Agent, or Firm*—Kenyon & Kenyon LLP

(57) ABSTRACT

The present invention provides processes for crystallization of macrolides, specifically pimecrolimus and tacrolimus.

25 Claims, No Drawings

PROCESSES FOR PRODUCING CRYSTALLINE MACROLIDES

RELATED APPLICATIONS

This application claims benefit of U.S. Provisional Patent Applications Nos. 60/632,372, filed Dec. 1, 2004, 60/633, 926, filed Dec. 6, 2004, 60/641,697, filed Jan. 5, 2005, 60/641,868, filed Jan. 5, 2005, 60/641,869, filed Jan. 5, 2005, 60/662,440, filed Mar. 16, 2005, 60/705,681, filed Aug. 3, 2005, and 60/709,160, filed Aug. 17, 2005, the contents of which are incorporated herein in their entirety by reference.

FIELD OF THE INVENTION

The present invention is directed to novel processes for the preparation of crystalline macrolides, pimecrolimus and tacrolimus in particular.

BACKGROUND OF THE INVENTION

Macrolides are multi-membered lactone rings having one or more deoxy sugars as substituents. Erythromycin, azithromycin, and clarithromycin are macrolides that have bacteriostatic and/or bactericidal activity. Ascomycin, tacrolimus, and Pimecrolimus are also macrolides.

Ascomycin is an immunomodulating macrolactam that reportedly blocks T-cell activation, inhibits cytokine release, and inhibits mast cell activation. "The mechanism of action of ascomycin is very similar to that of cyclosporin and of tacrolimus, although the three compounds have different chemical structures." C. E. Griffiths, Ascomycin: An Advance in the Management of Atopic Dermatitis. 144 Br. J. Dermatol., No. 4,679,679 (April 2001). Ascomycin is disclosed in U.S. Pat. No. 3,244,592, which describes the compound as an antifungal agent. The use of ascomycin as an immunosuppressant is disclosed in European Patent Application No. 323865.

Tacrolimus (FK 506) is a macrolide antibiotic that is also an immunosuppressive agent. More potent than cyclosporin, tacrolimus has a selective inhibitory effect on T-lymphocytes.

Rapamycin is an immunosuppressive lactam macrolide produceable, for example by *Streptomyces hygroscopicus*. The structure of rapamycin is given in Kesseler, H., et al.; 1993; Helv. Chim. Acta; 76:117. Rapamycin is an extremely potent immunosuppressant and has also been shown to have antitumor and antifungal activity. Its utility as a pharmaceutical, however, is restricted by its very low and variable bioavailability. Moreover, rapamycin is highly insoluble in aqueous media, e.g. water, making it difficult to formulate stable galenic compositions. Numerous derivatives of rapamycin are known. Rapamycin and its structurally similar analogues and derivatives are termed collectively herein as "rapamycins". On oral administration to humans, solid rapamycins, e.g. rapamycin, may not be absorbed to any significant extent into the bloodstream.

Pimecrolimus is an anti-inflammatory compound derived from ascomycin, which is produced by certain strains of *Streptomyces*. Pimecrolimus is sold in the United States under the brand name ELIDEL®, and is approved for use against atopic dermatitis. The systematic nane of Pimecrolimus is (1R,9S,12S,13R,14S,17R,18E,21S,23S,24R,25S, 27R)-12-[(1E)-2-{(1R,3R,4S)-4-chloro-3-methoxycyclohexyl}-1-methylvinyl]-17-ethyl-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone. Pimecrolimus is the 32-epichloro derivative of ascomycin. Its empirical formula is $C_{43}H_{68}ClNO_{11}$, and its molecular weight is 810.47.

The crystalline form of a solid chemical compound (or the lack of a crystalline form) affects many of the compound's properties that are important with respect to formulation as a pharmaceutical. Such properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

Another important property of a pharmaceutical compound that may depend on crystallinity is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The solid state form of a compound may also affect its behavior on compaction and its storage stability.

These practical physical characteristics are influenced by the conformation and orientation of molecules in the unit cell, which defines a particular crystalline form of a substance. These conformational and orientation factors in turn result in particular intramolecular interactions such that different crystalline forms may give rise to distinct spectroscopic properties that may be detectable by such analytical techniques as powder X-ray diffraction, solid state $^{13}$C NMR spectrometry, and infrared spectrometry. A particular crystalline form may also give rise to thermal behavior different from that of the amorphous material or another crystalline form. Thermal behavior is measured in the laboratory by such techniques as capillary melting point, thermogravimetric analysis (TGA), and differential scanning calorimetry (DSC), and can be used to distinguish some crystalline forms from others.

U.S. Pat. No. 6,423,722 discloses crystalline forms of pimecrolimus, such as form A, form B, etc.

The crystalline form of a solid chemical compound (or the lack of a crystalline form) affects many of the compound's properties that are important with respect to formulation as a pharmaceutical. Such properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important property of a pharmaceutical compound that may depend on crystallinity is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The solid state form of a compound may also affect its behavior on compaction and its storage stability.

These practical physical characteristics are influenced by the conformation and orientation of molecules in the unit cell, which defines a particular crystalline form of a substance. These conformational and orientation factors in turn result in particular intramolecular interactions such that different crystalline forms may give rise to distinct spectroscopic properties that may be detectable by such analytical techniques as powder X-ray diffraction, solid state $^{13}$C NMR spectrometry, and infrared spectrometry. A particular crystalline form may also give rise to thermal behavior different from that of the amorphous material or another crystalline form. Thermal behavior is measured in the laboratory by such techniques as capillary melting point, thermogravimetric analysis (TGA) and differential scanning calorimetry (DSC) and can be used to distinguish some crystalline forms from others.

The discovery of new crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

Thus, there is a need in the art for new methods for crystallization of macrolides.

SUMMARY OF THE INVENTION

In one embodiment the present invention provides a novel process for preparing crystalline macrolides comprising:
combining a macrolide with a first polar organic solvent to obtain a solution;
combining the solution with a second polar organic solvent and an antisolvent to form a mixture;
maintaining the mixture until the macrolide crystallizes; and
recovering the crystalline macrolide.

In another embodiment the present invention provides a novel process for preparing crystalline pimecrolimus comprising:
combining pimecrolimus with a first polar organic solvent to obtain a solution;
combining the solution with a second polar organic solvent and an antisolvent to form a mixture;
maintaining the mixture until the pimecrolimus crystallizes; and
recovering the crystalline pimecrolimus.

In yet another embodiment the present invention provides a novel process for preparing crystalline tacrolimus comprising:
combining tacrolimus with a first polar organic solvent to obtain a solution; combining the solution with a second polar organic solvent and an antisolvent to form a mixture;
maintaining the mixture until the tacrolimus crystallizes; and
recovering the crystalline tacrolimus.

Preferably, the crystalline tacrolimus obtained by the above process is characterized by a powder X-ray diffraction pattern having peaks at about 10.5, 11.3 and 13.8±0.2 degrees 2-theta.

Another embodiment of the present invention is a pharmaceutical formulation comprising a therapeutically effective amount of crystalline pimecrolimus or tacrolimus produced by the present invention, and an amount of pharmaceutically acceptable excipient.

DETAILED DESCRIPTION

As used herein, the term "room temperature" refers to a temperature of about 18° C. to about 25° C., preferably about 20° C. to about 22° C.

By "small amount" of polar solvent is meant a ratio of solvent mixture to polar solvent (or mixture of two or more polar solvents) of about 140/1 to about 636/1, preferably about 200/1 to about 500/1, even more preferably about 300/1 to about 350/1, on a volume/volume basis. Ratios of solvent mixture/polar solvent (or polar solvent mixture) that have been found to be suitable include: 140/1, 212/1, 300/1, 318/1, 325/1, 350/1, and 636/1.

Alternatively, a "small amount" can be considered with respect to the ratio of the molar equivalents of polar solvent (or polar solvent mixture) to macrolide. It has been found that as little as 0.5 molar equivalents of polar solvent with respect to macrolide results in the crystallization of the macrolide. Thus, it is within the scope of the present invention to add about 0.3, 0.4, 0.5, 0.6, 0.7, or 0.8 (or sometimes even more) molar equivalents of polar solvent (with respect to macrolide) in the processes of the present invention to effect dissolution of the macrolide.

In one embodiment the present invention provides a novel process for preparing crystalline macrolides comprising:
combining a macrolide with a first polar organic solvent to obtain a solution;
combining the solution with a second polar organic solvent and an antisolvent to form a mixture;
maintaining the mixture until the macrolide crystallizes; and
recovering the crystalline macrolide.

Preferably, the macrolide is selected from the group consisting of: rapamycin, everolimus, tacrolimus, ascomycin and pimecrolimus. Most preferably, the macrolide is pimecrolimus or tacrolimus.

Preferably, the first organic polar solvent in step a) is selected from the group consisting of: ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methy-ethyl ketone, and mixtures thereof. Most preferably, the solvent is ethyl acetate.

In order to obtain a clear solution, the temperature in step a) is elevated to not more than about 50° C.

Alternatively, a clear solution may be obtained by diluting or filtering out any particle. Filtration may be done through paper, glass fiber or other membrane material, or a clarifying agent such as celite. Depending upon the equipment used and the concentration and temperature of the solution, the filtration apparatus may need to be preheated to avoid premature crystallization.

Preferably, the antisolvent is selected from the group consisting of: cyclohexane, hexane, heptane, n-octane, iso-octane, and methylcyclohexane. Most preferably, the antisolvent is cyclohexane.

Optionally, the process may be performed without the antisolvent of step b).

Preferably, the second polar organic solvent is selected from the group consisting of: water, N,N-dimethylformamide, dimethylsulfoxide, dimethyl acetamide, N,N-diethylformamide, and mixtures thereof. More preferably, the polar solvent is selected from the group consisting of: water, N,N-dimethylformamide, and dimethylsulfoxide. Most preferably, the polar solvent is water or N,N dimethylformamide.

Optionally, the second polar organic solvent is added in a small amount.

Preferably, the antisolvent and the second polar organic solvent are added more or less simultaneously to the solution of tacrolimus in the first polar organic solvent.

Preferably, the reaction mixture in step (c) is maintained at a low temperature to induce crystallization. Preferably the reaction mixture is maintained at a temperature of about −15° C. to about 30° C. Preferably, the reaction mixture is maintained at a temperature of about 0° C. to about 8° C.

The crystallization is facilitated by initially using a concentrated solution of the macrolide. Preferably, the solution concentration is about 0.06 g/mL to about 0.8 g/mL. A high concentration also results in a higher yield.

In another embodiment the present invention provides a novel process for preparing crystalline pimecrolimus comprising:

combining pimecrolimus with a first polar organic solvent to obtain a solution;

combining the solution with a second polar organic solvent and an antisolvent to form a mixture;

maintaining the mixture until the pimecrolimus crystallizes; and recovering the crystalline pimecrolimus.

Preferably, the pimecrolimus crystallization process parameters are as described above.

In yet another embodiment the present invention provides a novel process for preparing crystalline tacrolimus comprising:

combining tacrolimus with a first polar organic solvent to obtain a solution;

combining the solution with a second polar organic solvent and an antisolvent to form a mixture;

maintaining the mixture until the tacrolimus crystallizes; and recovering the crystalline tacrolimus.

Preferably, the crystalline tacrolimus obtained by the above process is characterized by a powder X-ray diffraction pattern having peaks at about 10.5, 11.3 and 13.8±0.2 degrees 2-theta. The crystalline tacrolimus obtained by the above process may be further characterized by a powder X-ray diffraction having an additional peak at about 14.2±0.2 deg. 2-theta. The above crystalline tacrolimus may be even further characterized by powder X-ray diffraction having additional peaks at about 8.7, 15.4 and 19.1±0.2 deg. 2-theta.

Another embodiment of the present invention is a pharmaceutical formulation comprising a therapeutically effective amount of crystalline pimecrolimus or tacrolimus produced by the present invention, and an amount of pharmaceutically acceptable excipient.

"Therapeutically effective amount" means the amount of a crystalline form that, when administered to a patient for treating a disease or other undesirable medical condition, is sufficient to have a beneficial effect with respect to that disease or condition.

The "therapeutically effective amount" will vary depending on the crystalline form, the disease or condition and its severity, and the age, weight, etc., of the patient to be treated. Determining the therapeutically effective amount of a given crystalline form is within the ordinary skill of the art, and requires no more than routine experimentation.

Pharmaceutical formulations of the present invention contain the crystalline pimecrolimus or tacrolimus produced by the processes of the present invention. In addition to the active ingredient(s), the pharmaceutical formulations of the present invention may contain one or more excipients. Excipients are added to the formulation for a variety of purposes.

Diluents may be added to the formulations of the present invention. Diluents increase the bulk of a solid pharmaceutical composition, and may make a pharmaceutical dosage form containing the composition easier for the patient and caregiver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®, and starch.

Glidants can be added to improve the flowability of a non-compacted solid composition, and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion, and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance, and/or facilitate patient identification of the product and unit dosage level.

In liquid pharmaceutical compositions prepared using the crystalline pimecrolimus or tacrolimus produced by the processes of the present invention, pimecrolimus or tacrolimus and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form, and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The oral dosage form of the present invention is preferably in the form of an oral capsule having a dosage of about 10 mg to about 160 mg, more preferably from about 20 mg to about 80 mg, and most preferably capsules of 20, 40, 60, and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin, and, optionally, contain a plasticizer such as glycerin and sorbitol, and an opacifying agent or colorant.

A composition for tableting or capsule filling may be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Instruments

The crystalline pimecrolimus and tacrolimus, produced by the methods of the present invention can be analyzed by Powder X-ray diffraction (PXRD) was performed on an X-Ray powder diffractometer, ARL, θ-θgoniometer, Cu-tube, solid state detector with Peltier cooling. The sample holder was a round standard aluminum sample holder with round zero background. Scanning parameters: Step mode or continuous Scan, Rate: 3 deg./min. The crystalline form of Tacrolimus can be analyzed also in a formulation, by the same XRD method. The scan rate maybe lowered for increase sensitivity, as known by any skilled in the art person The crystalline pimecrolimus and tacrolimus can also be analyzed by thermal analysis, which can be carried out by differential scanning calorimetry (DSC) and by thermogravimetric analysis (TGA). DSC thermograms can be obtained on a DSC822$^e$ Mettler Toledo instrument. Sample weight: 3-5 mg; Heating rate: 10° C./min; Number of holes in the crucible: 3. TGA thermograms can be obtained on a Mettler TGA/SDTA 851 instrument using a standard Alumina pan. Sample weight: 7-15 mg; Heating rate: 10° C./min.

Example 1

Process for the Preparation of Crystalline Pimecrolimus

Pimecrolimus (1.5 g) is dissolved in ethyl acetate (10 ml), and evaporated to dryness. This process is repeated twice. The evaporated oily material is dissolved in ethyl acetate (3 ml). Cyclohexane (18 ml) is added to the solution. Water (0.033 ml) is added in small portions during 3 hours. The mixture is stirred for an hour at room temperature. The crystalline product is filtered, washed with cyclohexane (3 ml), and dried for 1.5 hours at 40° C. under reduced pressure. Crystalline Pimecrolimus is obtained.

Example 2

Process for the Preparation of Crystalline Pimecrolimus

Pimecrolimus (6 g) is dissolved in ethyl acetate (48 ml), and evaporated to reduced volume (9 ml). The mixture is stirred at room temperature for an hour then is kept at 0 to 8° C. for 24 hours. The crystalline product thus formed is filtered and washed with cyclohexane (18 ml), and dried for 1.5 hours at 50° C. under reduced pressure. Crystalline Pimecrolimus is obtained.

Example 3

Process for the Preparation of Crystalline Pimecrolimus

Pimecrolimus (6 g) is dissolved in ethyl acetate (60 ml), and evaporated to dryness. This process is repeated twice. The evaporated oily material is dissolved in ethyl acetate (6 ml). Cyclohexane (36 ml) and dimethyl formamide (0.12 ml) are added to the solution, and it is stirred for 1.5 hours at room temperature. The crystalline product is filtered and washed with cyclohexane (18 ml) and dried for 1 hour at 60° C. under reduced pressure. Crystalline Pimecrolimus is obtained.

Example 4

Process for the Preparation of Crystalline Pimecrolimus

Pimecrolimus (6 g) is dissolved in ethyl acetate (60 ml), and evaporated to dryness. This process is repeated twice. The evaporated oily material is dissolved in ethyl acetate (6 ml). Cyclohexane (66 ml) and dimethyl sulfoxide (0.24 ml) are added to the solution, and it is stirred for 1.5 hours at room temperature. The crystalline product is filtered and washed with cyclohexane (18 ml), and dried for 1 hour at 70° C. under reduced pressure. Crystalline Pimecrolimus is obtained.

Example 5

Process for the Preparation of Crystalline Pimecrolimus

Pimecrolimus (6 g) is dissolved in ethyl acetate (60 ml), and evaporated to dryness. This process is repeated twice. The evaporated oily material is dissolved in ethyl acetate (6 ml). Cyclohexane (36 ml) and mixture of dimethyl formamide (0.06 ml) and water (0.06 ml) is added to the solution. The mixture is stirred for 1.5 hours at room temperature. The crystalline product is filtered and washed with cyclohexane (18 ml), and dried for 1 hour at 70° C. under reduced pressure. Crystalline Pimecrolimus is obtained.

Example 6

Process for the Preparation of a Crystalline Form of Tacrolimus

Crystalline Tacrolimus (13 g) was dissolved in ethyl acetate (39 ml) and evaporated to dryness. This process was repeated twice. The evaporated oily or foamy material was dissolved in ethyl acetate (13 ml). Cyclohexane (78 ml) was added to the solution. Water (0.28 ml) was added in small portions during 3 hours. The mixture was stirred for an hour at room temperature. The crystalline product was filtered and washed with cyclohexane (13 ml) and dried for 16 hours at 40° C. under reduced pressure. 9.49 g was obtained, of Tacrolimus crystalline form, characterized by powder X-ray diffraction having peaks at about 10.5, 11.3 and 13.8±0.2 degrees 2-theta.

Example 7

Process for the Preparation of a Crystalline Form of Tacrolimus

Tacrolimus (2 g) was dissolved in ethyl acetate (6 ml) and evaporated to dryness. This process was repeated twice. The evaporated oily material was dissolved in ethyl acetate (2 ml). Cyclohexane (10 ml) and dimethyl formamide (0.088 ml) were added to the solution and it was crystallized for 16 hours at 0-5° C. The crystalline product was filtered and washed with cyclohexane (6 ml) and dried for 5 hours at 50° C. under reduced pressure. 1.28 g was obtained, of Tacrolimus crystalline form, characterized by powder X-ray diffraction having peaks at about 10.5, 11.3 and 13.8±0.2 degrees 2-theta.

Example 8

Process for the Preparation of a Crystalline Form of Tacrolimus

Tacrolimus (2 g) was dissolved in ethyl acetate (6 ml) and evaporated to dryness. This process was repeated twice. The evaporated oily material was dissolved in ethyl acetate (2 ml). Cyclohexane (12 ml) and dimethyl sulfoxide (0.044 ml) were added to the solution and it was stirred for 16 hours at 0-5° C. The crystalline product thus formed was filtered and washed with cyclohexane (6 ml) and dried for 5 hours at 50° C. under reduced pressure. 1.57 g was obtained, of Tacrolimus crystalline form, characterized by powder X-ray diffraction having peaks at about 10.5, 11.3 and 13.8±0.2 degrees 2-theta.

Example 9

Process for the Preparation of a Crystalline Form of Tacrolimus

Tacrolimus (2 g) was dissolved in ethyl acetate (6 ml) and evaporated to dryness. This process was repeated twice. The evaporated oily material was dissolved in ethyl acetate (2 ml). Cyclohexane (12 ml) and a mixture of dimethyl formamide (0.044 ml) and water (0.022 ml) were added to the solution. The mixture was stirred for 16 hours at room temperature. The crystalline product thus formed was filtered and washed with cyclohexane (6 ml) and dried for 5 hours at 50° C. under reduced pressure. 1.11 g was obtained, of Tacrolimus crystalline form, characterized by powder X-ray diffraction having peaks at about 10.5, 11.3 and 13.8±0.2 degrees 2-theta.

What is claimed:

1. A process for crystallizing a macrolide comprising:
   crystallizing a macrolide from a first solvent, a small amount of a second polar organic solvent, and an antisolvent,
   wherein the first solvent is selected from the group consisting of ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone, and mixtures thereof, wherein the second polar organic solvent is selected from the group consisting of N,N-dimethylformamide, dimethylsulfoxide, dimethyl acetamide, N,N-diethylformamide, and mixtures thereof, and wherein the macrolide is selected from the group consisting of tacrolimus, ascomycin, and pimecrolimus.

2. The process of claim 1, wherein the first solvent, the second solvent, and the antisolvent are all different.

3. The process of claim 1, wherein the first solvent is ethyl acetate.

4. The process of claim 1, wherein the macrolide concentration is about 0.06 to about 0.8 g per ml first solvent.

5. The process of claim 1, wherein the antisolvent is selected from the group consisting of cyclohexane, hexane, heptane, n-octane, iso-octane, and methylcyclohexane.

6. The process of claim 1, wherein the antisolvent is cyclohexane.

7. The process of claim 1, wherein the second solvent is N,N-dimethylformamide.

8. The process of claim 1, wherein the macrolide is dissolved in the first solvent prior to admixing the dissolved macrolide with the second solvent or the antisolvent.

9. The process of claim 8, wherein the mixture of the first solvent and the macrolide is heated to a temperature of not more than about 50° C.

10. The process of claim 8, wherein the antisolvent and the second solvent are added simultaneously to the solution of macrolide in the first solvent.

11. The process of claim 1, wherein the crystallization of macrolide occurs at a temperature of about −15° C. to about 30° C.

12. The process of claim 11, wherein the crystallization of macrolide occurs at a temperature of about 0° C. to about 8° C.

13. The process of claim 1, wherein the macrolide is pimecrolimus.

14. The process of claim 1, wherein the macrolide is tacrolimus.

15. The process of claim 14, wherein the crystalline tacrolimus is characterized by powder X ray diffraction pattern having peaks at about 10.5, 11.3, and 13.8±0.2 degrees 2-theta.

16. The process of claim 1, wherein the volume ratio of the total amount of the first solvent and the antisolvent to the second solvent is about 140/1 to about 636/1.

17. The process of claim 16, wherein the volume ratio of the total amount of the first solvent and the antisolvent to the second solvent is about 200/1 to about 500/1.

18. The process of claim 17, wherein the volume ratio of the total amount of the first solvent and the antisolvent to the second solvent is about 300/1 to about 350/1.

19. The process of claim 1, wherein the volume ratio of the antisolvent to the first solvent is about 5:1 to about 11:1.

20. The process of claim 1, wherein the volume ratio of the antisolvent to the first solvent is about 6:1.

21. A process for crystallizing a macrolide comprising:
crystallizing a macrolide from a first solvent, an antisolvent, and a sufficient amount of a second solvent to induce crystallization, wherein the first solvent is selected from the group consisting of ethyl acetate, methanol, ethanol, n-propanol, isopropanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone, and mixtures thereof, wherein the second solvent is selected from the group consisting of N,N-dimethylformamide, dimethylsulfoxide, dimethyl acetamide, N,N-diethylformamide, and mixtures thereof, and wherein the macrolide is selected from the group consisting of tacrolimus, ascomvcin, and pimecrolimus.

22. The process of claim 21, wherein the macrolide is tacrolimus.

23. A process for crystallizing a macrolide comprising:
crystallizing a macrolide from a first solvent, a small amount of water, and an antisolvent, wherein the first solvent is selected from the group consisting of ethyl acetate, methanol, ethanol, n-propanol, isopropanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone, and mixtures thereof, and wherein the macrolide is selected from the group consisting of tacrolimus, ascomvcin, and pimecrolimus.

24. The process of claim 23, wherein the macrolide is tacrolimus.

25. The process of claim 4, wherein the macrolide concentration is about 0.5 to about 1.0 g per ml of first solvent.

* * * * *